United States Patent
Chen et al.

(10) Patent No.: US 11,905,229 B2
(45) Date of Patent: *Feb. 20, 2024

(54) METHOD FOR SYNTHESIZING DICLOFENAC SODIUM

(71) Applicant: Fudan University, Shanghai (CN)

(72) Inventors: Fener Chen, Shanghai (CN); Dang Cheng, Shanghai (CN); Lulu Wang, Shanghai (CN); Ge Meng, Shanghai (CN); Yingtang Ning, Shanghai (CN); Zedu Huang, Shanghai (CN)

(73) Assignee: Fudan University, Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/172,414

(22) Filed: Feb. 22, 2023

(65) Prior Publication Data

US 2023/0234911 A1 Jul. 27, 2023

(30) Foreign Application Priority Data

Feb. 25, 2022 (CN) .......................... 202210178956.5

(51) Int. Cl.
*C07C 227/18* (2006.01)
*B01J 21/02* (2006.01)

(52) U.S. Cl.
CPC ............. *C07C 227/18* (2013.01); *B01J 21/02* (2013.01)

(58) Field of Classification Search
None
See application file for complete search history.

(56) References Cited

U.S. PATENT DOCUMENTS

| | | |
|---|---|---|
| 3,558,690 A | 1/1971 | Sallmann et al. |
| 4,978,773 A | 12/1990 | Grafe et al. |

FOREIGN PATENT DOCUMENTS

| | | |
|---|---|---|
| CN | 1580039 A | 2/2005 |
| CN | 108947861 A | 12/2018 |
| DE | 1815802 A1 | 7/1969 |
| EP | 0380712 A1 | 8/1990 |
| GB | 1132128 A | 10/1968 |
| NL | 6604752 A | 10/1966 |
| WO | 9222522 A1 | 12/1992 |

OTHER PUBLICATIONS

Shengqian Fei et al., Synthesis of antipyretic, analgesic and anti-inflammatory drug diclofenac sodium, Chinese Journal of Pharmaceutical Industry, 1979, No. 11, pp. 14-19.
Fener Chen et al., Synthesis of Diclofenac Sodium by Rearrangement II .,Chinese Journal of Pharmaceuticals, 1998, No. 8, pp. 339-341.
Bingchang Qin et al.,Study on the synthetic process of diclofenac, Applied Chemical Industry, 2008 No. 3 issue, pp. 275-278,297.

*Primary Examiner* — Sudhakar Katakam
*Assistant Examiner* — Jennifer C Sawyer

(57) ABSTRACT

A method of synthesizing diclofenac sodium, including: subjecting aniline and chloroacetic acid to amidation to obtain 2-chloro-N-phenylacetamide; subjecting 2-chloro-N-phenylacetamide and 2,6-dichlorophenol to condensation reaction to obtain 2-(2,6-dichlorophenoxy)-N-phenylacetamide; subjecting 2-(2,6-dichlorophenoxy)-N-phenylacetamide to Smiles rearrangement in the presence of an inorganic base to obtain N-(2,6-dichlorophenyl)-2-hydroxy-N-phenylacetamide; subjecting N-(2,6-dichlorophenyl)-2-hydroxy-N-phenylacetamide and thionyl chloride to chlorination to obtain N-(2,6-dichlorophenyl)-2-chloro-N-phenylacetamide; subjecting N-(2,6-dichlorophenyl)-2-chloro-N-phenylacetamide to Friedel-Crafts alkylation in the presence of a Lewis acid catalyst to obtain 1-(2,6-dichlorophenyl)-1,3-dihydro-2H-indol-2-one; and subjecting 1-(2,6-dichlorophenyl)-1,3-dihydro-2H-indol-2-one to hydrolysis in the presence of an inorganic base to obtain diclofenac sodium.

10 Claims, 2 Drawing Sheets

METHOD FOR SYNTHESIZING DICLOFENAC SODIUM

CROSS-REFERENCE TO RELATED APPLICATIONS

This application claims the benefit of priority from Chinese Patent Application No. 202210178956.5, filed on Feb. 25, 2022. The content of the aforementioned application, including any intervening amendments thereto, is incorporated herein by reference in its entirety.

TECHNICAL FIELD

This application relates to pharmaceutical engineering, and more particularly to a method for synthesizing diclofenac sodium.

BACKGROUND

Diclofenac sodium, which was developed by Ciba-Geigy Ltd. and came into the market in 1974, is a non-steroidal anti-inflammatory drug derived from phenylacetic acid. It is usually used as an antipyretic-analgesic drug in clinic to relieve pains caused by rheumatoid arthritis, lupus erythematosus, neuritis, cancer and surgery, and the fever. The diclofenac sodium mainly plays a role in inhibiting the in-vivo synthesis of prostaglandins. Compared with other anti-inflammatory and analgesic drugs, the diclofenac sodium has a stronger anti-inflammatory activity (2-2.5 times stronger than indomethacin, and 20-50 times stronger than aspirin). Furthermore, the diclofenac sodium experiences rapid absorption after oral administration, and fast elimination rate, and will not cause accumulation effect after long-term administration. The diclofenac sodium is widely recognized as an anti-rheumatic drug due to small individual differences. The diclofenac sodium is structurally shown as follows:

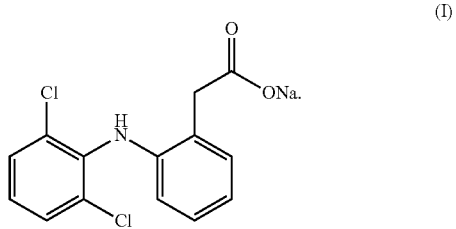

(I)

U.S. Pat. No. 3,558,690, GB patent No. 1132128 and a non-patent literature (Fei Shengqian & Cai Yunming. "Synthesis of diclofenac sodium for antipyretic and anti-inflammatory drug" [J]. Chinese Journal of Pharmaceuticals, 1979 (10), 14-18) disclose a preparation process of diclofenac sodium, in which o-(chloro)benzoic acid, as a staring material, is subjected to Ullmann condensation and decarboxylation to prepare a key intermediate 2,6-dichloroaniline, which further undergoes acylation, ring-closing reaction, ring cleavage reaction and salt formation to obtain the diclofenac sodium (I). The above-mentioned method has readily-available raw materials, but it also struggles with complicated process, use of highly toxic and corrosive compounds, serious environmental pollution and low total yield.

NL patent No. 6604752 and JP patent No. 23418 prepare 2,6-di-chlorodiphenylamine in one step through the Ullmann condensation reaction between bromobenzene and 2,6-dichloroaniline (about 50% yield). This synthesis process is generally accompanied by the occurrence of some by-products difficult to be eliminated, such as N-phenyl-2-chloro-6-bromoaniline, which may cause side effects such as stomach ulcers.

DE patent No. 1815802 synthesizes an intermediate N-arylindole-2,3-dione through Stolle synthesis in the presence of oxalyl chloride as an acylation reagent, which further undergoes reduction and hydrolysis to prepare diclofenac sodium. This method has high yield, but it involves the use of oxalyl chloride which is expensive, highly toxic, corrosive and irritating, heavy pollution, high operation requirements, and complicated procedures.

It has also been disclosed by a Japanese patent that o-chlorobenzoic acid is condensed with 2,6-dichloroaniline, and then the condensation product is converted into diclofenac sodium in the presence of a carbon source such as diazomethane and sodium cyanide. However, this method is extremely dangerous due to the use of highly-toxic diazomethane or sodium cyanide, and will cause serious environmental pollution, and thus is not suitable for industrial production.

EP patent No. 0380712 and WO patent No. 022522 employ aniline as raw materials to prepare diclofenac sodium through acylation, etherification and Chapman rearrangement. Chen Fener et al. (Chen fener & Deng yan. Study on synthesis process of diclofenac sodium II. Substitution of acetanilide rearrangement[J]. Chinese Journal of Pharmaceuticals, 1998, 29(8):339), U.S. Pat. No. 4,978,773 and Qin Bingchang et al. (Qin bingchang et al. Study on the synthetic process of diclofenac sodium[J]. Applied Chemical Industry, 2008, 37(3):275-278) employ 2,6-di-chlorodiphenylamine and chloroacetyl chloride as raw materials to prepare diclofenac sodium through acylation, intramolecular Friedel-Crafts alkylation and ring-opening reaction. This method is one of the main synthesis routes for diclofenac sodium, but it is also limited by complicated operation, poor atomic economy and serious pollution.

Chinese patent application publication No. 1580039 A employs cyclohexanone as raw material to prepare diclofenac sodium through chlorination, carboxylation, hydrogenation, condensation, aromatization and salt formation. This method has high yield, but it also involves toxic, corrosive and irritating materials such as chlorine gas, chloroacetyl chloride and organic phosphorus, heavy pollution, high operation requirements, and cumbersome procedures.

Chinese patent application publication No. 108947861A employs phenylacetic acid as raw material to prepare diclofenac sodium through nitration, reduction, amidation, condensation, rearrangement and hydrolysis. However, this method is limited by cumbersome procedures and the use of corrosive and irritating nitration reagents and expensive palladium catalysts, and thus is not suitable for industrial production.

In view of the defects in the existing synthesis approaches, it is urgently needed to develop a novel strategy of synthesizing diclofenac sodium with high yield, desirable atomic economy, less pollution, low cost and easy operation.

SUMMARY

An object of the disclosure is to provide a method for synthesizing diclofenac sodium with high atomic economy, simple and environmentally-friendly process, high overall yield, and low cost to overcome the defects in the prior art.

Technical solutions of the present disclosure are described as follows.

This application provides a method for synthesizing diclofenac sodium, comprising:
(S1) subjecting aniline and chloroacetic acid to amidation in an organic solvent in the presence of a boric acid catalyst to obtain 2-chloro-N-phenylacetamide (II);
(S2) subjecting 2-chloro-N-phenylacetamide (II) and 2,6-dichlorophenol to condensation reaction in the presence of potassium carbonate and a phase transfer catalyst to obtain 2-(2,6-dichlorophenoxy)-N-phenylacetamide (III);
(S3) subjecting 2-(2,6-dichlorophenoxy)-N-phenylacetamide (III) to Smiles rearrangement in the presence of a basic catalyst to obtain N-(2,6-dichlorophenyl)-2-hydroxy-N-phenylacetamide (IV);
(S4) subjecting N-(2,6-dichlorophenyl)-2-hydroxy-N-phenylacetamide (IV) and thionyl chloride to chlorination in the presence of a catalyst to obtain N-(2,6-dichlorophenyl)-2-chloro-N-phenylacetamide (V);
(S5) subjecting N-(2,6-dichlorophenyl)-2-chloro-N-phenylacetamide (V) to Friedel-Crafts alkylation in the presence of a Lewis acid catalyst to obtain 1-(2,6-dichlorophenyl)-1,3-dihydro-2H-indol-2-one (VI); and
(S6) subjecting 1-(2,6-dichlorophenyl)-1,3-dihydro-2H-indol-2-one (VI) to hydrolysis in the presence of an inorganic base to obtain diclofenac sodium (I);
as shown in the following reaction scheme:

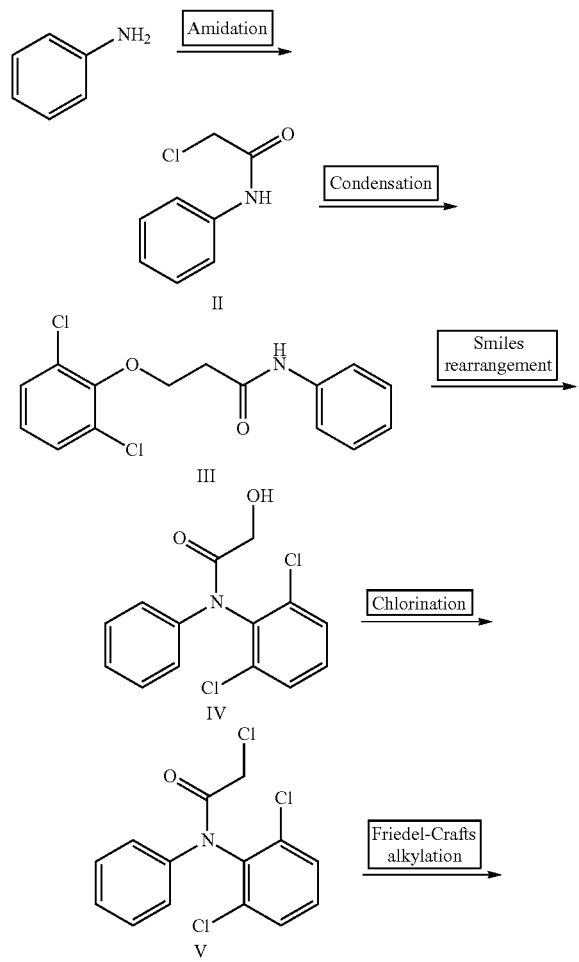

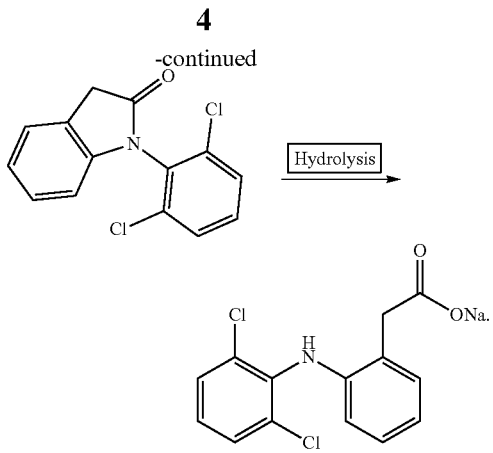

The total yield can reach 74% as calculated by aniline, and the product quality satisfies the standards of US Pharmacopeia (USP), British Pharmacopoeia (BP), Japan Pharmaceutical Agency and Chinese Pharmacopoeia.

In some embodiments, in step (S1), the boric acid catalyst is fluoro-substituted arylboronic acid, o-halogenated arylboronic acid, aminoboronic acid, boric acid or boronate ester.

In some embodiments, in step (S1), a molar ratio of aniline to chloroacetic acid to the boric acid catalyst is 1:(1-5):(0.001-0.5).

In some embodiments, in step (S1), the organic solvent is chlorobenzene, toluene, xylene, dichlorobenzene, mesitylene, acetonitrile or 1-butanol.

In some embodiments, in step (S1), the amidation is performed at 0-150° C. for 1-20 h.

In some embodiments, in step (S2), the phase transfer catalyst is polyethylene glycol 400 (PEG-400), polyethylene glycol 600 (PEG-600), benzyltriethylammonium chloride (TEBAC) or tetrabutylammonium bromide.

In some embodiments, in step (S2), a molar ratio of 2-chloro-N-phenylacetamide (II) to 2,6-dichlorophenol to potassium carbonate to the phase transfer catalyst is 1:(0.5-2):(1-5):(0.001-0.5).

In some embodiments, in step (S2), the condensation reaction is performed in an organic solvent selected from the group consisting of chlorobenzene, toluene, xylene, dichlorobenzene, mesitylene, acetonitrile and 1-butanol.

In some embodiments, in step (S2), the condensation reaction is performed at 80-160° C. for 2-15 h.

In some embodiments, in step (S3), the basic catalyst is an inorganic base or an organic base; the inorganic base is selected from the group consisting of sodium hydroxide, calcium hydroxide, sodium carbonate, sodium bicarbonate, potassium carbonate, potassium bicarbonate and sodium hydride; and the organic base is selected from the group consisting of triethylamine, pyridine, sodium methoxide, lithium diisopropylamide and 1,8-diazabicyclo[5.4.0]undec-7-ene.

In some embodiments, in step (S3), a molar ratio of 2-(2,6-dichlorophenoxy)-N-phenylacetamide (III) to the basic catalyst is 1:(0.001-20).

In some embodiments, in step (S3), the Smiles rearrangement is performed in an organic solvent selected from the group consisting of N,N-dimethylformamide, dimethyl sulfoxide, methanol, ethanol, toluene, acetonitrile, ethyl acetate and acetone.

In some embodiments, in step (S3), the Smiles rearrangement is performed at 0-100° C. for 0.5-10 h.

In some embodiments, in step (S4), the catalyst is pyridine, N,N-dimethylaniline, triethylamine or N,N-dimethylformamide.

In some embodiments, in step (S4), a molar ratio of N-(2,6-dichlorophenyl)-2-hydroxy-N-phenylacetamide (IV) to thionyl chloride to the catalyst is 1:(1-4):(0.001-0.5).

In some embodiments, in step (S4), the chlorination is performed in an organic solvent selected from the group consisting of N,N-dimethylformamide, dimethyl sulfoxide, thionyl chloride, toluene, acetonitrile, dichloromethane, 1,2-dichloroethane, ethyl acetate and acetone.

In some embodiments, in step (S4), the chlorination is performed at 10-100° C. for 0.5-10 h.

In some embodiments, in step (S5), the Lewis acid catalyst is selected from the group consisting of aluminum chloride, ferric chloride, zinc chloride, zinc bromide and tin tetrachloride.

In some embodiments, in step (S5), a molar ratio of N-(2,6-dichlorophenyl)-2-chloro-N-phenylacetamide (V) to the Lewis acid catalyst is 1:(0.5-5).

In some embodiments, in step (S5), the Friedel-Crafts alkylation is performed in the presence of an organic solvent selected from the group consisting of dichloromethane, 1,2-dichloroethane, chlorobenzene, toluene, xylene, dichlorobenzene, 1-butanol or diphenyl ether.

In some embodiments, in step (S5), the Friedel-Crafts alkylation is preformed in a solvent-free manner.

In some embodiments, in step (S5), the Friedel-Crafts alkylation is performed at 50-200° C. for 1-10 h.

In some embodiments, in step (S6), the inorganic base is sodium carbonate, sodium bicarbonate or sodium hydroxide.

In some embodiments, in step (S6), the hydrolysis is performed in a phase transfer catalyst-free manner.

In some embodiments, in step (S6), the hydrolysis is performed in the presence of a phase transfer catalyst to promote the hydrolysis; and the phase transfer catalyst is benzyltriethylammonium chloride or tetrabutylammonium bromide.

In some embodiments, in step (S6), a molar ratio of 1-(2,6-dichlorophenyl)-1,3-dihydro-2H-indol-2-one (VI) to the inorganic base to the phase transfer catalyst is 1:(0.1-10):(0-0.5).

In some embodiments, in step (S6), the hydrolysis is performed in an organic solvent selected from the group consisting of toluene, xylene, diphenyl ether, methanol and ethanol.

In some embodiments, in step (S6), the hydrolysis is performed in a solvent-free manner.

In some embodiments, in step (S6), the hydrolysis is performed at 10-130° C. for 1-10 h.

Compared to the prior art, this application has the following beneficial effects.

This application employs chloroacetic acid as an acylation reagent, which has low toxicity, irritation and corrosiveness and low labor protection requirements compared with chloroacetyl chloride used in the prior art. With respect to the amidation reaction, the boronic acid catalyst contributes to great catalytic activity, and high conversion rate. Moreover, the boronic acid catalyst can be recycled, and is environmentally friendly.

In the prior art, 2-(2,6-dichlorophenoxy)-N-phenylacetamide (III) will be hydrolyzed into 2,6-di-chlorodiphenylamine after the Smiles rearrangement, and subsequently, it is required to use chloroacetyl chloride again for amidation, resulting in poor atomic economy, serious pollution and high labor protection requirements. In the synthesis route provided herein, the Smiles rearrangement is controlled to generate an intermediate N-(2,6-dichlorophenyl)-2-hydroxy-N-phenylacetamide (IV), and avoid the hydrolysis side reaction, avoiding the repeated use of highly-toxic chloroacetyl chloride and improving atomic economy.

The synthesis method provided herein has readily-available raw materials, high yield (74%), good atomic economy, low cost and low operation requirement. Moreover, this synthesis route is environmentally friendly, and the product quality satisfies the standards of USP, BP, Japan Pharmaceutical Agency and Chinese Pharmacopoeia. Therefore, this synthesis method has overcome the defects in the prior art, and is suitable for industrial production.

DETAILED DESCRIPTION OF EMBODIMENTS

Figure 1:
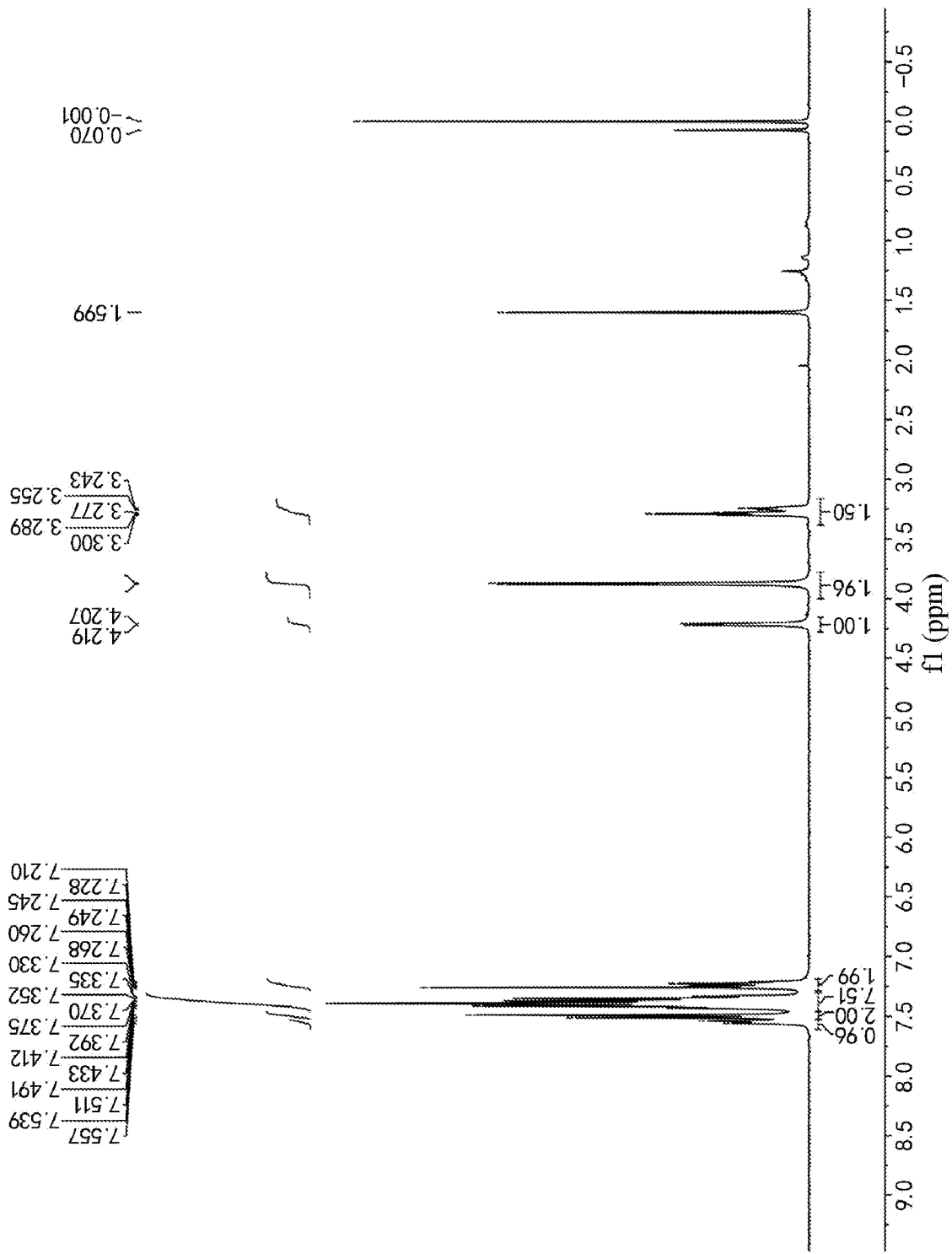
FIG. 1 is a $^1$H nuclear magnetic resonance spectrum ($^1$H-NMR) of N-(2,6-dichlorophenyl)-2-hydroxy-N-phenylacetamide.
Figure 2:
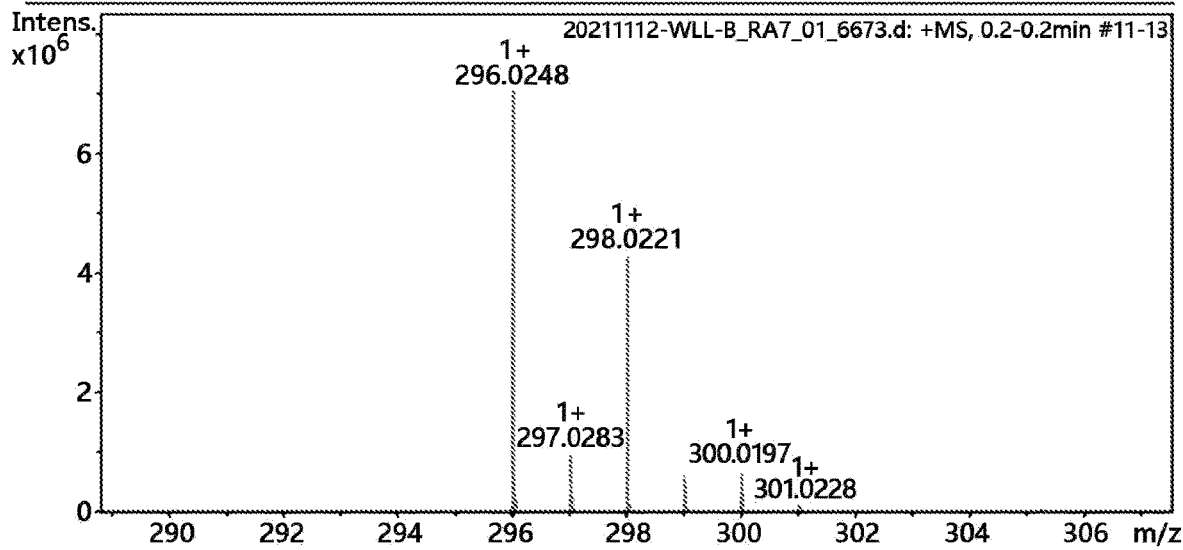
FIG. 2 is a high-resolution mass spectrum of N-(2,6-dichlorophenyl)-2-hydroxy-N-phenylacetamide.
Figure 2:
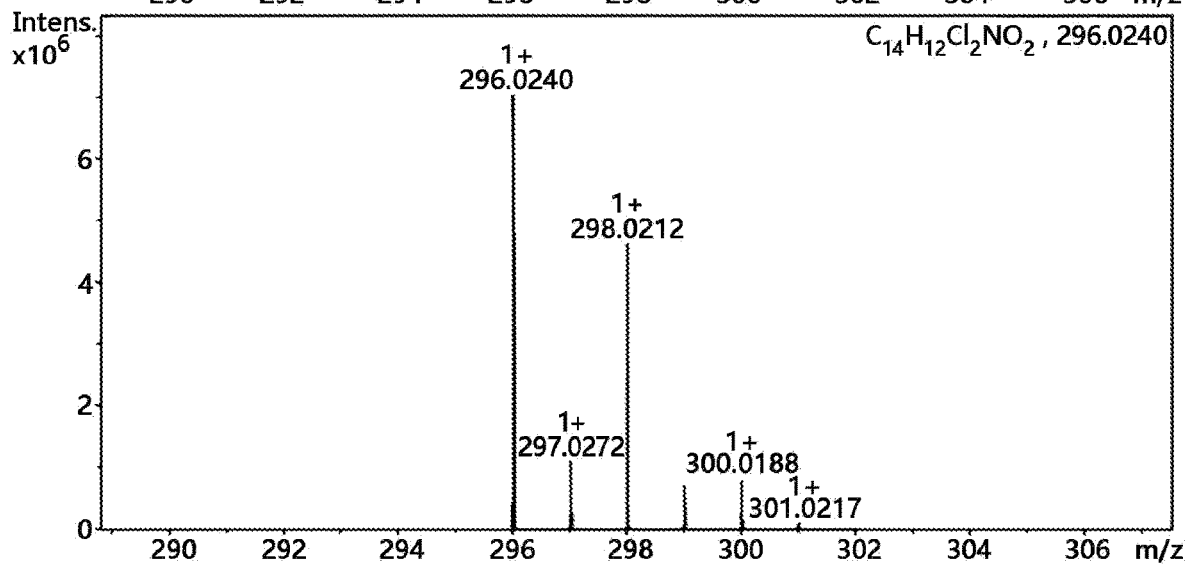

In order to clearly illustrate the objects and technical solutions of the present disclosure, the present disclosure will be described below in detail with reference to the embodiments and accompanying drawings. It should be noted that described below are merely illustrative of the present disclosure, and not intended to limit the present disclosure.

Preparation of 2-chloro-N-phenylacetamide (II)

Example 1

10.395 g (0.11 mol) of chloroacetic acid, 61.83 mg (0.001 mol) of boric acid and 200 mL of toluene were added to a dry reaction flask, to which 9.313 g (0.1 mol) of aniline was slowly added. The reaction mixture was heated to 130° C., and refluxed under stirring for 6 h. After the reaction was confirmed by thin-layer chromatography (TCL) to be complete, the reaction mixture was neutralized with sodium bicarbonate, and then subjected to extraction. An organic phase was collected, and subjected to washing with a 10% sodium sulfate solution, concentration and vacuum distillation to obtain 16.28 g of a yellow solid as 2-chloro-N-phenylacetamide (II) (yield: 96%; and m.p.: 85-87° C.).

Example 2

14.17 g (0.15 mol) of chloroacetic acid, 61.83 mg (0.001 mol) of boric acid and 200 mL of toluene were added to a dry reaction flask, to which 9.313 g (0.1 mol) of aniline was slowly added. The reaction mixture was heated to 130° C., and refluxed under stirring for 6 h. After the reaction was confirmed by TCL to be complete, the reaction mixture was neutralized with sodium bicarbonate, and then subjected to extraction. An organic phase was collected, and subjected to subjected to washing with a 10% sodium sulfate solution, concentration and vacuum distillation to obtain 16.62 g of a yellow solid as 2-chloro-N-phenylacetamide (II) (yield: 98%; and m.p.: 85-87° C.).

Example 3

51.97 g (0.55 mol) of chloroacetic acid, 618.3 mg (0.01 mol) of boric acid and 200 mL of toluene were added to a dry reaction flask, to which 46.565 g (0.5 mol) of aniline was slowly added. The reaction mixture was heated to 140° C., and refluxed under stirring for 12 h. After the reaction was confirmed by thin-layer chromatography (TCL) to be complete, the reaction mixture was neutralized with sodium bicarbonate. An organic phase was collected, and subjected to washing with a 10% sodium sulfate solution, concentration and vacuum distillation to obtain 81.41 g of a yellow solid as 2-chloro-N-phenylacetamide (II) (yield: 96%; and m.p.: 85-87° C.).

Preparation of
2-(2,6-dichlorophenoxy)-N-phenylacetamide (III)

Example 4

16.69 g (0.1 mol) of 2-chloro-N-phenylacetamide (II), 16.63 g (0.1 mol) of 2,6-dichlorophenol, 27.64 g (0.2 mol) of potassium carbonate, 0.4 g of PEG-400 and 160 mL of xylenes were added to a reaction flask. The reaction mixture was heated to 150° C., and refluxed under stirring for 2 h. After the reaction was confirmed by TCL to be complete, the reaction mixture was neutralized with dilute hydrochloric acid, and then subjected to extraction. An organic phase was collected, and subjected to drying with anhydrous sodium sulfate and vacuum distillation to obtain 29.46 g of a yellow solid as 2-(2,6-dichlorophenoxy)-N-phenylacetamide (III) (yield: 95%; and m.p.: 78-80° C.).

Example 5

33.38 g (0.2 mol) of 2-chloro-N-phenylacetamide (II), 33.26 g (0.2 mol) of 2,6-dichlorophenol, 69.1 g (0.5 mol) of potassium carbonate, 1.8 g of PEG-600 and 320 mL of xylenes were added to a reaction flask. The reaction mixture was heated to 150° C., and refluxed under stirring for 4 h. After the reaction was confirmed by TCL to be complete, the reaction mixture was neutralized with dilute hydrochloric acid, and then subjected to extraction. An organic phase was collected, and subjected to drying with anhydrous sodium sulfate and vacuum distillation to obtain 59.55 g of a yellow solid as 2-(2,6-dichlorophenoxy)-N-phenylacetamide (III) (yield: 96%; and m.p.: 78-80° C.).

Preparation of
N-(2,6-dichlorophenyl)-2-hydroxy-N-phenylacetamide
(IV)

Example 6

31.02 g (0.1 mol) of 2-(2,6-dichlorophenoxy)-N-phenylacetamide (III) and 10.60 g (0.1 mol) of anhydrous sodium carbonate were added to a reaction flask. The reaction mixture was added with 100 mL of toluene under a nitrogen atmosphere, and heated to 60° C. for reaction. After the reaction was confirmed by TCL to be complete, the reaction mixture was neutralized with ammonium chloride, and then subjected to extraction. An organic phase was collected, and subjected to drying with anhydrous sodium sulfate and vacuum distillation to obtain 26.06 g of a yellow solid as N-(2,6-dichlorophenyl)-2-hydroxy-N-phenylacetamide (IV) (yield: 85%; and m.p.: 112-114° C.).

Example 7

31.02 g (0.1 mol) of 2-(2,6-dichlorophenoxy)-N-phenylacetamide (III) and 13.82 g (0.1 mol) of anhydrous potassium carbonate were added to a reaction flask. The reaction mixture was added with 100 mL of toluene under a nitrogen atmosphere, and heated to 70° C. for reaction. After the reaction was confirmed by TCL to be complete, the reaction mixture was neutralized with ammonium chloride, and then subjected to extraction. An organic phase was collected, and subjected to drying with anhydrous sodium sulfate and vacuum distillation to obtain 26.65 g of a yellow solid as N-(2,6-dichlorophenyl)-2-hydroxy-N-phenylacetamide (IV) (yield: 88%; and m.p.: 112-114° C.).

Example 8

31.02 g (0.1 mol) of 2-(2,6-dichlorophenoxy)-N-phenylacetamide (III) and 5.3 g (0.05 mol) of anhydrous sodium carbonate were added to a reaction flask. The reaction mixture was added with 100 mL of toluene under a nitrogen atmosphere, and heated to 70° C. for reaction. After the reaction was confirmed by TCL to be complete, the reaction mixture was neutralized with ammonium chloride, and then subjected to extraction. An organic phase was collected, and subjected to drying with anhydrous sodium sulfate and vacuum distillation to obtain 26.65 g of a yellow solid as N-(2,6-dichlorophenyl)-2-hydroxy-N-phenylacetamide (IV) (yield: 88%; and m.p.: 112-114° C.).

Preparation of
N-(2,6-dichlorophenyl)-2-chloro-N-phenylacetamide
(V)

Example 9

59.23 g (0.2 mol) of N-(2,6-dichlorophenyl)-2-hydroxy-N-phenylacetamide (IV), 47.59 g (0.4 mol) of thionyl chloride and 100 mL of dichloromethane were added to a dry reaction flask, to which 0.202 g (0.002 mol) of triethylamine was slowly dropwise added under stirring. The reaction mixture was reacted under reflux for 4 h. After the reaction was confirmed by TCL to be complete, the reaction mixture was subjected to filtration to remove insoluble substances, and vacuum distillation to recover thionyl chloride, so as to obtain 61.97 g of a yellow solid as N-(2,6-dichlorophenyl)-2-chloro-N-phenylacetamide (V) (yield: 99% and m.p.: 142-143° C.).

Example 10

59.23 g (0.2 mol) of N-(2,6-dichlorophenyl)-2-hydroxy-N-phenylacetamide (IV) and 100 mL of thionyl chloride were added to a dry reaction flask, to which 0.202 g (0.002 mol) of triethylamine was slowly dropwise added under stirring. The reaction mixture was reacted under reflux for 3 h. After the reaction was confirmed by TCL to be complete, the reaction mixture was subjected to filtration to remove insoluble substances, and vacuum distillation to recover thionyl chloride, so as to obtain 59.47 g of a yellow solid as N-(2,6-dichlorophenyl)-2-chloro-N-phenylacetamide (V) (yield: 95% and m.p.: 142-143° C.).

Example 11

29.62 g (0.1 mol) of N-(2,6-dichlorophenyl)-2-hydroxy-N-phenylacetamide (IV), 23.79 g (0.2 mol) of thionyl chloride and 100 mL of dichloroethane were added to a dry reaction flask, to which 1.01 g (0.01 mol) of triethylamine was slowly dropwise added under stirring. The reaction mixture heated to 50° C. to react for 1 h. After the reaction was confirmed by TCL to be complete, the reaction mixture was subjected to filtration to remove insoluble substances, and vacuum distillation to recover thionyl chloride, so as to obtain 30.67 g of a yellow solid as N-(2,6-dichlorophenyl)-2-chloro-N-phenylacetamide (V) (yield: 98% and m.p.: 142-143° C.).

Preparation of 1-(2,6-dichlorophenyl)-1,3-dihydro-2H-indol-2-one (VI)

Example 12

31.3 g (0.1 mol) of N-(2,6-dichlorophenyl)-2-chloro-N-phenylacetamide (V) were added to a dry reaction flask. The reaction mixture was added with 26.67 g (0.2 mol) of aluminum chloride under a nitrogen atmosphere, and heated to 160° C. to react at a melt state for 6 h. After the reaction was confirmed by TCL to be complete, the reaction mixture was poured into ice water to obtain a solid product, and then filtered. The filtrate was subjected to reverse extraction and concentration with dichloromethane, combined with the solid product, washed with deionized water and dried with anhydrous sodium sulfate to obtain 26.96 g of a brownish yellow solid as 1-(2,6-dichlorophenyl)-1,3-dihydro-2H-indol-2-one (VI) (yield: 96%; and m.p.: 124-125° C.).

Example 13

31.3 g (0.1 mol) of N-(2,6-dichlorophenyl)-2-chloro-N-phenylacetamide (V) and 50 mL of chlorobenzene were added to a dry reaction flask. The reaction mixture was stirred, added with 26.67 g (0.2 mol) of aluminum chloride under a nitrogen atmosphere, and heated to 160° C. to react for 4 h. After the reaction was confirmed by TCL to be complete, the reaction mixture was slowly added with dilute hydrochloric acid, and then subjected to extraction. An organic phase was collected, and subjected to drying with solid sodium sulfate, filtration and vacuum distillation to obtain 19.46 g of a brownish yellow solid as 1-(2,6-dichlorophenyl)-1,3-dihydro-2H-indol-2-one (VI) (yield: 97%; and m.p.: 124-125° C.).

Preparation of Diclofenac Sodium (I)

Example 14

16 g (0.4 mol) of sodium hydroxide and 38 mL of water were added to a reaction flask. The reaction mixture was stirred for dissolution, cooled, added with 27.7 g (0.1 mol) of 1-(2,6-dichlorophenyl)-1,3-dihydro-2H-indol-2-one (VI), 100 mL of xylene and 2.28 g (0.01 mol) of TEBAC under stirring, and refluxed under heating for 6 h. Then, the reaction mixture was cooled to room temperature, and subjected to vacuum distillation to recover solvent, recrystallization with 100 mL of water and decolorization with activated carbon to obtain 28.53 g of a white solid as diclofenac sodium (I) (yield: 95%; and m.p.: 283-284° C.).

Example 15

16 g (0.4 mol) of sodium hydroxide and 38 mL of water were added to a reaction flask. The reaction mixture was stirred for dissolution, cooled, added with 27.7 g (0.1 mol) of 1-(2,6-dichlorophenyl)-1,3-dihydro-2H-indol-2-one (VI) and 100 mL of methanol under stirring, and refluxed under heating for 6 h. Then, the reaction mixture was cooled to room temperature, and subjected to vacuum distillation to recover methanol, recrystallization with 100 mL of water and decolorization with activated carbon to obtain 30.12 g of a white solid as diclofenac sodium (I) (yield: 96%; and m.p.: 283-284° C.).

What is claimed is:

1. A method for synthesizing diclofenac sodium, comprising:
    (S1) subjecting aniline and chloroacetic acid to amidation in an organic solvent in the presence of a boric acid catalyst to obtain 2-chloro-N-phenylacetamide (II);
    (S2) subjecting 2-chloro-N-phenylacetamide (II) and 2,6-dichlorophenol to condensation reaction in the presence of potassium carbonate and a phase transfer catalyst to obtain 2-(2,6-dichlorophenoxy)-N-phenylacetamide (III);
    (S3) subjecting 2-(2,6-dichlorophenoxy)-N-phenylacetamide (III) to Smiles rearrangement in the presence of a basic catalyst to obtain N-(2,6-dichlorophenyl)-2-hydroxy-N-phenylacetamide (IV);
    (S4) subjecting N-(2,6-dichlorophenyl)-2-hydroxy-N-phenylacetamide (IV) and thionyl chloride to chlorination in the presence of a catalyst to obtain N-(2,6-dichlorophenyl)-2-chloro-N-phenylacetamide (V);
    (S5) subjecting N-(2,6-dichlorophenyl)-2-chloro-N-phenylacetamide (V) to Friedel-Crafts alkylation in the presence of a Lewis acid catalyst to obtain 1-(2,6-dichlorophenyl)-1,3-dihydro-2H-indol-2-one (VI); and
    (S6) subjecting 1-(2,6-dichlorophenyl)-1,3-dihydro-2H-indol-2-one (VI) to hydrolysis in the presence of an inorganic base to obtain diclofenac sodium (I).

2. The method of claim 1, wherein in step (S1), the boric acid catalyst is fluoro-substituted arylboronic acid, o-halogenated arylboronic acid, aminoboronic acid, boric acid or boronate ester.

3. The method of claim 1, wherein in step (S1), a molar ratio of aniline to chloroacetic acid to the boric acid catalyst is 1:(1-5):(0.001-0.5);
    the organic solvent is chlorobenzene, toluene, xylene, dichlorobenzene, mesitylene, acetonitrile or 1-butanol; and
    the amidation is performed at 0-150° C. for 1-20 h.

4. The method of claim 1, wherein in step (S2), the phase transfer catalyst is polyethylene glycol 400 (PEG-400), polyethylene glycol 600 (PEG-600), benzyltriethylammonium chloride (TEBAC) or tetrabutylammonium bromide;
    a molar ratio of 2-chloro-N-phenylacetamide (II) to 2,6-dichlorophenol to potassium carbonate to the phase transfer catalyst is 1:(0.5-2):(1-5):(0.001-0.5);
    the condensation reaction is performed in an organic solvent selected from the group consisting of chlorobenzene, toluene, xylene, dichlorobenzene, mesitylene, acetonitrile and 1-butanol; and
    the condensation reaction is performed at 80-160° C. for 2-15 h.

5. The method of claim 1, wherein in step (S3), the basic catalyst is an inorganic base or an organic base; the inorganic base is selected from the group consisting of sodium hydroxide, calcium hydroxide, sodium carbonate, sodium bicarbonate, potassium carbonate, potassium bicarbonate and sodium hydride; and the organic base is selected from the group consisting of triethylamine, pyridine, sodium methoxide, lithium diisopropylamide and 1,8-diazabicyclo[5.4.0]undec-7-ene;
    a molar ratio of 2-(2,6-dichlorophenoxy)-N-phenylacetamide (III) to the basic catalyst is 1:(0.001-20);
    the Smiles rearrangement is performed in an organic solvent selected from the group consisting of N,N- dimethylformamide, dimethyl sulfoxide, methanol, ethanol, toluene, acetonitrile, ethyl acetate and acetone; and the Smiles rearrangement is performed at 0-100° C. for 0.5-10 h.

6. The method of claim 1, wherein in step (S4), the catalyst is pyridine, N,N-dimethylaniline, triethylamine or N,N-dimethylformamide;
- a molar ratio of N-(2,6-dichlorophenyl)-2-hydroxy-N-phenylacetamide (IV) to thionyl chloride to the catalyst is 1:(1-4):(0.001-0.5);
- the chlorination is performed in an organic solvent selected from the group consisting of N,N-dimethylformamide, dimethyl sulfoxide, thionyl chloride, toluene, acetonitrile, dichloromethane, 1,2-dichloroethane, ethyl acetate and acetone; and
- the chlorination is performed at 10-100° C. for 0.5-10 h.

7. The method of claim 1, wherein in step (S5), the Lewis acid catalyst is selected from the group consisting of aluminum chloride, ferric chloride, zinc chloride, zinc bromide and tin tetrachloride;
- a molar ratio of N-(2,6-dichlorophenyl)-2-chloro-N-phenylacetamide (V) to the Lewis acid catalyst is 1:(0.5-5);
- the Friedel-Crafts alkylation is performed in a solvent-free manner or in the presence of an organic solvent selected from the group consisting of dichloromethane, 1,2-dichloroethane, chlorobenzene, toluene, xylene, dichlorobenzene, 1-butanol or diphenyl ether; and
- the Friedel-Crafts alkylation is performed at 50-200° C. for 1-10 h.

8. The method of claim 1, wherein in step (S6), the inorganic base is sodium carbonate, sodium bicarbonate or sodium hydroxide; and
- the hydrolysis is performed in the presence of a phase transfer catalyst; a molar ratio of 1-(2,6-dichlorophenyl)-1,3-dihydro-2H-indol-2-one (VI) to the inorganic base to the phase transfer catalyst is 1:(0.1-10):(0-0.5); and the phase transfer catalyst is benzyltriethylammonium chloride or tetrabutylammonium bromide.

9. The method of claim 1, wherein in step (S6), the hydrolysis is performed in a solvent-free manner or in an organic solvent selected from the group consisting of toluene, xylene, diphenyl ether, methanol and ethanol.

10. The method of claim 1, wherein in step (S6), the hydrolysis is performed at 10-130° C. for 1-10 h.

* * * * *